United States Patent
Lê et al.

(10) Patent No.: US 7,510,574 B2
(45) Date of Patent: Mar. 31, 2009

(54) IMPLANTABLE DEVICE AS ORGAN VALVE REPLACEMENT

(75) Inventors: Trong-Phi Lê, Hamburg (DE); Johannes Jung, Karlsruhe (DE)

(73) Assignee: pfm, Produkte fur die Medizin AG, Cologne (DE)

( * ) Notice: Subject to any disclaimer, the term of this patent is extended or adjusted under 35 U.S.C. 154(b) by 297 days.

(21) Appl. No.: 10/901,324

(22) Filed: Jul. 28, 2004

(65) Prior Publication Data

US 2005/0060029 A1 Mar. 17, 2005

Related U.S. Application Data (60) Provisional application No. 60/490,784, filed on Jul. 29, 2003.

(51) Int. Cl.
*A61F 2/24* (2006.01)

(52) U.S. Cl. .................................. 623/2.14; 623/23.68

(58) Field of Classification Search ........ 623/1.24–41.2
See application file for complete search history.

(56) References Cited

U.S. PATENT DOCUMENTS

| | | | |
|---|---|---|---|
| 3,714,671 A * | 2/1973 | Edwards et al. ............. | 623/2.19 |
| 4,816,029 A | 3/1989 | Penny, III et al. | |
| 5,728,158 A | 3/1998 | Lau et al. | |
| 5,855,597 A | 1/1999 | Jayaraman | |
| 6,290,728 B1 | 9/2001 | Phelps et al. | |
| 6,425,916 B1 * | 7/2002 | Garrison et al. ............. | 623/2.11 |
| 6,440,164 B1 | 8/2002 | DiMatteo et al. | |
| 6,458,153 B1 * | 10/2002 | Bailey et al. ................ | 623/1.24 |
| 6,482,228 B1 * | 11/2002 | Norred ....................... | 623/2.17 |
| 6,508,835 B1 | 1/2003 | Shaolian et al. | |
| 6,752,828 B2 * | 6/2004 | Thornton ................... | 623/1.24 |
| 7,201,771 B2 * | 4/2007 | Lane ........................... | 623/2.14 |
| 2002/0138135 A1 | 9/2002 | Duerig et al. | |
| 2002/0193871 A1 | 12/2002 | Beyersdorf et al. | |
| 2003/0153943 A1 * | 8/2003 | Michael et al. ............. | 606/200 |
| 2004/0102855 A1 * | 5/2004 | Shank ....................... | 623/23.68 |
| 2005/0283231 A1 * | 12/2005 | Haug et al. ................ | 623/2.11 |
| 2006/0106450 A1 * | 5/2006 | Ben Muvhar ............... | 623/1.15 |
| 2006/0212110 A1 * | 9/2006 | Osborne et al. ............ | 623/1.24 |

FOREIGN PATENT DOCUMENTS

| | | |
|---|---|---|
| DE | 34 41 478 A1 | 5/1987 |
| DE | 691 01 385 T2 | 6/1994 |
| DE | 196 24 948 A1 | 1/1998 |

(Continued)

*Primary Examiner*—Suzette J Gherbi
(74) *Attorney, Agent, or Firm*—Baker & Daniels LLP (57) ABSTRACT

An implantable device for use in a human and/or animal body for replacement of an organ valve. The device has an elongate main body having a first end and a second end provided with openings, and a membrane element provided with at least one opening. The device has, in a first operating state (primary form), a large ratio of length to transverse extent along an axis, and, in a second operating state (secondary form), a smaller ratio of length to transverse extent along an axis. The device is reversibly convertible from the secondary form into the primary form by application of force against elastic material forces. At least one of the two ends of the main body has an outwardly protruding anchoring portion for anchoring the device in the organ and/or a vessel.

34 Claims, 9 Drawing Sheets

FOREIGN PATENT DOCUMENTS

| | | |
|---|---|---|
| DE | 101 18 944 A2 | 10/2002 |
| DE | 101 21 210 A1 | 11/2002 |
| EP | 0 592 410 B1 | 10/1995 |
| EP | 0 928 606 A1 | 7/1999 |
| EP | 1 057 460 A1 | 6/2000 |
| EP | 1 044 663 A2 | 10/2000 |
| EP | 1 057 460 A1 | 12/2000 |
| EP | 1302179 A2 | 4/2003 |
| JP | 2001000460 | 1/2001 |
| WO | WO 97/46177 | 12/1997 |

\* cited by examiner

IMPLANTABLE DEVICE AS ORGAN VALVE REPLACEMENT

The invention relates to an implantable device for use in the human and/or animal body for replacement of an organ valve, with an elongate main body having a first end and a second end provided with openings, and with a membrane element provided with at least one opening, said device in a first operating state (primary form) having a large ratio of length to transverse extent along an axis and, in a second operating state (secondary form), having a smaller ratio of length to transverse extent along the axis, said device being able to be converted reversibly from the secondary form to the primary form by application of a force counter to elastic material forces, and the invention also relates to a method for producing an implantable device of this kind.

Implantable devices of this kind for replacement of an organ valve in the human and/or animal body are known in the prior art. It was previously customary in particular to replace heart valves by performing open-heart surgery, which is an operation not without risks, especially in elderly patients. Devices for heart valve replacement were therefore developed which can be brought to the correct position in the heart via a catheter and without open-heart surgery. From EP 0 592 410, for example, it is known to provide a compressible elastic valve which is arranged on an elastic stent, the commissural points of the elastic compressible valve being applied on the cylinder surface of the elastic stent. The elastic compressible valve is a biological, trilobate valve. The stent consists of a stainless steel wire which is folded in a number of loops and bent in a circle and welded together. The stent comprises two or more closed rings which are connected to one another in order to form a cylindrical structure. Three of the loops in the outer ring are designed with a greater height than the other loops, so as to form apices to which the commissural points of the biological valve are attached. The cylindrical surface of the stent can also be of a closed design. On account of the tubular or annular shape of the stent, only a relatively poor anchoring is possible in the implantation area, in particular in the aorta and the heart.

A better anchoring for a heart valve replacement is described in DE 101 21 210 A1. According to said document, an intraluminal anchoring element is designed deviating from the cylinder shape such that, in its position of use, it is connected to the aorta with a shape fit, at least in some areas. According to said document, the intraluminal anchoring element therefore has radially extending widened parts at the heart outlet (behind the original aortic valve). Furthermore, it is curved to adapt to the curved path of the aorta. The anchoring element is additionally made up of, for example, a lattice-shaped, loop-shaped or screw-shaped thread structure or filaments and can comprise several meandering, ring-forming thread structures. The individual ring-forming structures are interconnected by adhesive bonding, soldering, welding, etc. In this design of a heart valve replacement, the disadvantage is that the anchoring element has a very long design, that is to say has to be inserted very deep into a blood vessel or the heart. Openings are admittedly provided for the origins of different coronary arteries, but the length of the anchoring element can have the effect that some of these openings are covered by the anchoring element, so that blockage of the blood flow or clogging of the origins may arise there.

EP 1 057 460 A1 and the abstract of JP 2001000460 A disclose the provision of a heart valve replacement device which has a stent, said stent being expandable in the radial direction of the blood vessel, and a biological valve being secured on the stent. The stent valve arrangement is arranged on the expandable part of a balloon catheter and introduced into the human body. The stent is made up of a multiplicity of portions made of wire. The individual wire portions are welded together. By means of the balloon catheter, the stent is expanded to the desired diameter at the implantation site. This is done in two stages. After expansion of the stent at the implantation site, the diameter of the balloon catheter is reduced again and the catheter is removed. The pulmonary valve replacement device remains in the pulmonary artery, touching the artery wall. A disadvantage of this heart valve replacement device is that a balloon catheter has to be used to expand the stent. In addition, the stent is intended to sit in the vessel or artery solely on the basis of its expanded shape. It has been shown, however, that with this form of a heart valve replacement problems can arise because of shifting of the stent inside the vessel, and, in particular, inexact positioning may lead to blocking of the origins of the coronary vessels, with the result of at least partial closure of these origins and, consequently, blockage of the blood flow. Problems also arise, where incorrect positioning is concerned, in that although the stent is expanded by means of the balloon, its diameter cannot be reduced again.

From U.S. Pat. No. 5,855,597 it is also known to cut out star-shaped elements and join these together to form a stent. An aortic valve replacement made of a flexible, biocompatible material is inserted into a central opening of the star-shaped elements which have been joined together. The stent is brought to the desired implantation site via a catheter system. Although the star shape does provide a hold inside the patient's aorta, there is also a risk of injury occurring there, particularly if the blood vessel is slightly damaged, in particular perforatable, on account of the age or state of health of the patient.

U.S. Pat. No. 6,482,228 B1, for example, discloses an aortic valve replacement which comprises a stent and, distinct from this, but connected to it, a rotor-shaped valve replacement. The latter is arranged over the original valve. The stent consists of several joined-together rings of wires which have been bent in an undulating line. A disadvantage of this design proves to be the structure of the aortic valve replacement, with provision of a stent with distinct rotor-shaped element for arrangement behind the natural aortic valve. On the one hand, this is very complex, and, on the other hand, there is the risk of the rotor coming loose from the stent. Moreover, it is arranged inside the aorta substantially without any further holding by the stent, secured only in the longitudinal direction. The aortic valve replacement therefore does not represent a secure and stable unit.

For heart valve replacement, the prior art also includes annular devices which, at three places, have support posts drawn out from the ring. These can either be loop-shaped, as is disclosed in WO 97/46177, or made of a solid material, as is disclosed for example in U.S. Pat. No. 4,816,029, DE 196 24 948 A1 and DE 35 41 478 A1. However, not all of these annular heart valve replacement devices can be implanted via a catheter since they cannot be collapsed to a sufficiently small size.

The object of the present invention is to develop an implantable device for replacement of an organ valve in such a way that the aforementioned disadvantages no longer occur, and in particular to permit especially good and stable anchoring of the device at the implantation site in the organ and/or vessel in the area of the natural valve, and in this way to create a device which is as inexpensive as possible to produce.

For an implantable device according to the preamble of Claim 1, the object is achieved by the fact that at least one of the two ends of the main body has an outwardly protruding anchoring portion for anchoring the device in the organ and/or a vessel. For the main body of an implantable organ valve replacement device, the object is achieved by the fact that the main body is made substantially in one piece. For a method for producing such an implantable device, the object is achieved by the fact that a main body is cut and/or punched from a material section and/or separated from it by another method of separation, the resulting main body material section is bent to form a substantially cylindrically bent body and is connected at its longitudinal edges, and a membrane element is inserted into the substantially cylindrical main body and connected to the latter. Further developments of the invention are defined in the dependent claims.

By these means, an implantable device for replacement of an organ valve is created with which, by using protruding anchoring portions at both ends of the main body, it is possible to obtain a particularly good hold at these two ends in a vessel and/or organ. When the implantable device is in fact used as a heart valve replacement device, one end with a protruding anchoring portion can extend for example into the left ventricle and secure itself there, and the other end with the other protruding anchoring portion of the main body can be used for clamping to the wall of the aorta. In this way, the implantable device and in particular the main body can be made much shorter than is possible for example in the case of the stent according to DE 101 21 210 A1. Since the main body can also be converted reversibly from a primary form to a secondary form, it can be brought to the implantation site without any problem via a catheter. When it slides out of the catheter, the implantable device deploys from the primary form to the secondary form, whereupon the diameter of the main body increases and as a result the length is in general slightly reduced. The possibility of reversible conversion from the primary form to the secondary form, and vice versa from the secondary form to the primary form, makes it possible, in contrast to the stent according to EP 1 057 460 A1, to retract the device into the catheter if, during implantation, it is decided that the device is not properly positioned, that is to say in particular the implantable device is not properly positioned with respect to the origins of the coronary vessels and/or the natural heart valve and the aorta and ventricle. Using a main body designed substantially in one piece reduces the production outlay, since the very elaborate joining together of individual filaments or wire loops is avoided and the material section, once bent, only has to be joined together along one edge in the longitudinal direction. By producing a main body made of only one piece, the latter is also made more secure against breaking in the area of weld points between individual wires. Such a breaking apart can in fact lead to a situation in which sharp-edged areas protrude from a stent and can damage or perforate the wall, in particular of the aorta. With a one-piece design, the structure of the main body can also be made more uniform than is possible when joining together individual annular elements, as is described in the prior art.

The protruding anchoring portion is preferably provided extending all around the circumference of the main body. Alternatively, however, individual protruding anchoring portions can also be provided on the circumference of the main body. One or other variant will be preferred depending on the implantation site, and the choice will in particular be made depending on the available space and possible constrictions in a vessel caused by calcification, etc.

The device preferably has areas of different stiffness. It is particularly preferable for an area of lesser stiffness to be arranged between areas of greater stiffness. The area of lesser stiffness is particularly preferably provided in the main body outside the anchoring portions. By providing areas of different stiffness, bends at the implantation site can be imitated. These bends, for example in the aorta, can be followed particularly easily in areas of lesser stiffness of the device. In order to guarantee a good hold at the implantation site, the areas of the anchoring portions, that is to say the end areas of the main body, preferably have a greater stiffness than one or more portions arranged between them. Several areas of different stiffness can also be provided along the length of the main body if this is required by the external circumstances, in particular in the aorta or in the ventricle. The distribution of the different degrees of stiffness along the main body can thus also be adapted to the particular patient and to the spatial circumstances prevailing in the heart or at the implantation site.

In principle, it is possible to tailor the implantable device to the particular patient and/or to provide a standard format which can be used for the majority of patients. A basic format can also be provided in particular with areas that can be changed in variable ways, thus once again permitting adaptation to the majority of the exceptions. In this way, the costs involved in producing the implantable device are also reduced, because special customized configurations are extremely rare.

One or more guide openings are preferably provided for the passage of guide wires for implantation of the device. The at least one guide opening is particularly preferably arranged near to the membrane element. The at least one guide opening preferably has a diameter substantially corresponding to the opening width of the origins of the coronary arteries to be spanned in the implanted state of the device. The provision of guide wires for implantation of the device proves to be particularly advantageous since in this way it is possible to better direct the device during the implantation. When the implantable device is provided as a replacement for a heart valve, in particular the aortic valve, origins of the coronary arteries lie in the area of the valve, and these should be neither completely nor partially closed by the device since, if this happened, the passage of blood would no longer be possible or would be severely restricted, leading to serious health problems for the patient. By providing at least two guide openings near to the membrane element, the origins of the right coronary artery and of the left coronary artery can be framed by the guide openings.

For implanting the device, the guide wires can first be guided or threaded through the guide openings of the main body. The guide wires can then be advanced further by a probe as far as the implantation site in the heart and at least partially pushed into the coronary vessels. The implantable device is then advanced in the primary form, via a catheter, into the body of the patient and as far as the implantation site in the heart, and is pushed out of the catheter there and expanded. With the aid of the guide wires, the device is oriented with respect to the origins of the coronary vessels from the heart. The fact that the guide wires are guided into the coronary vessels permits a particularly simple and exact alignment of the guide openings of the main body of the implantable device with respect to these vessels. In addition to the guide openings, the implantable device can also have one or more additional openings, particularly in an area which, after implantation of the device, covers the origins of the coronary arteries. If one or more additional openings are provided on the main body or the device, the guide openings can also be made smaller because then they do not necessarily cover the origins of the coronary arteries. However, if they do so, they are preferably provided with a diameter corresponding to the opening width of the origins of the coronary arteries.

The device is preferably provided, particularly in the area of the main body, with markings which can be detected by imaging techniques. In this way, it is possible, during the implantation procedure, to monitor the positioning, particularly with respect to the origins of the coronary vessels, via a monitor or the like. Particularly suitable techniques include radiography or magnetic resonance tomography, which are able to display an axially accurate position of the implantable device, especially an aortic valve replacement, in the body of the patient. The markings can be provided at different locations on the main body or device, particularly also on the guide wires and in the area of the openings or guide openings.

The device is preferably pushed so far into the area of a heart valve, in particular an aortic valve, that the natural valve is pressed against the vessel wall and held there by the device. In this connection, it would in principle even be possible to introduce a further implantable device into an already implanted device, in which case the membrane element of the initially implanted device would also be pressed against the wall of the main body. Such introduction of a further implantable device into an already implanted device could prove useful, for example, in the event of deteriorating stability and mobility of the membrane element. It is also possible in principle, after an old natural valve has first been removed, in particular by surgery, to introduce an implantable device with membrane element as valve replacement at this location. In the event of severe calcification of the natural valve, it may prove advantageous to remove the latter completely since, in these cases, it has usually become completely unable to move. In this case it would otherwise be quite difficult to press the natural valve against the vessel wall. In addition, a constriction would remain in this area, which is also an undesirable state of affairs because it means a reduced cross section of flow and, consequently, an increase in pressure, and thus brings with it disadvantages for the patient's health.

The at least one guide wire and/or the implantable device is particularly preferably introduced into the body via the carotid aorta or axillary artery. In this way, the chosen implantation route covers a very short distance, in contrast to the implantation routes in the prior art, in which implantation in each case takes place through introduction of a catheter in the patient's groin region. This is the case in particular in DE 101 21 210 A1.

The main body of the device is preferably oriented in such a way that the anchoring portion protruding at the first end extends into the ventricle, in particular the left ventricle, and the anchoring portion protruding at the second end clamps onto the vessel wall, in particular the wall of the aorta. This permits a particularly good hold and a stable configuration. The respective dimensions of the anchoring portions can also be chosen differently on an individual basis, depending on the anatomy of the particular patient. The extent by which the anchoring portions protrude can also be chosen on an individual basis. In principle, however, it is also possible to achieve standardization in which the anchoring portions protrude to such an extent, and have such dimensions, that the vast majority of patients can be fitted with this kind of main body or implantable device.

The at least one guide wire is preferably threaded through the main body and/or arranged on the outside of the main body. For the implantation procedure, the nature of the arrangement of the guide wires on the main body of the implantable device can also be made dependent on the particular conditions of the patient. To the extent that retraction of the guide wires, when they are arranged on the outside of the main body, does not prove practical because of the fragility of the vessel in the area of the implantation site, the guide wire is preferably guided through the main body from the inside.

The implantable device particularly preferably has a main body which is cut and/or punched from a material section or separated from the latter by another method of separation. In this way, any desired cutting can be obtained and reproduced. Adaptation to the individual circumstances in the body of the patient can also be easily made by simple modification of the cutting. The cutting can in particular be controlled by computer, coupled with data from a measurement system and/or with the measurement system itself for measuring the implantation site by radiography, tomography, ultrasound, etc., in order to permit individual adaptation to the individual patient.

The material section preferably comprises parallel cuts and, alternating with these and adjoining them, obliquely extending cuts. Cuts extending transversely with respect to the parallel cuts are particularly preferably provided in order to produce areas of different stiffness. By providing parallel cuts, it is possible to produce net structures and meshes, in combination with the alternating obliquely extending cuts. The obliquely extending cuts in each case form the transition from one mesh to another, which in the prior art is produced by soldering, welding or similar. In some areas it is possible to provide parallel cuts and cuts arranged transversely with respect to these, which are positioned between two obliquely arranged cuts so that a weakening is obtained in the folded-out main body. In this way, an area of lesser stiffness can be produced which makes it easier to curve the main body. The material section is preferably configured to produce a continuous net structure of the substantially cylindrical main body, in particular with different mesh sizes. The cutting length can be varied and results in different mesh sizes. The length of the obliquely arranged cuts also influences the mesh size of individual meshes.

At its ends, the material section preferably has widened, rounded cut elements for producing atraumatic ends for the main body. In this way it is possible to avoid damage to the vessel walls in the end area of the main body, that is to say in the area of the protruding anchoring portions. In principle, another design is also possible, for example the provision of a ring which, upon expansion of the main body, deploys along with it.

Holes acting as guide openings and/or additional openings are preferably provided in the area of the obliquely extending cuts. The holes can also be provided in the other areas of the material section, but the area of the obliquely extending cuts, which form bridges, is particularly suitable for this purpose because of its width and its later spacing after expansion. Depending on the size of the holes and as a function of their shape, it is possible to make individual adaptations to the origins of the coronary arteries and also to the guide wires.

It proves particularly expedient if the membrane element for the implantable device has a ring portion and, connected to this, a valve portion. The valve portion preferably comprises three sail elements. A natural valve can in particular be simulated in this way. Provision of a ring portion permits a good anchoring on the main body of the implantable device. The main body is preferably made of a biocompatible material, in particular a metal or a metal alloy, in particular stainless steel, or a plastic such as polycarbonate, in particular a shape-memory material such as nitinol. The membrane element is preferably made of a synthetic or biological material, in particular polyurethane. Main body and membrane element can be connected to one another in a detachable or non-detachable manner. The connection of main body and membrane element can therefore be effected particularly preferably by adhesive bonding, welding, sewing, melting, or immersion, or by another joining technique. The ring portion of the membrane element is preferably chosen so wide that a good hold on the main body is permitted. Since the membrane element is generally made of a very thin material, the ring portion can, for example, be applied as a thin tube onto the main body or inserted into the latter. In this respect, immersion of the main body or application of a thin membrane portion onto the inside or outside of the main body are particularly suitable. In this way, protection is also achieved against the membrane element slipping relative to the main body.

To produce different degrees of stiffness, the material of the main body is particularly preferably treated, at least in one area, by chemical and/or mechanical means, in particular by etching, electropolishing, micro-sectioning or otherwise. Therefore, in addition to weakening of the material of the main body, it is in this way possible to produce different degrees of stiffness in the main body so as to be able to better adapt it to the natural shape of the aorta and ventricle.

To create biological stability, the membrane element can be provided with a coating. When a polyurethane is used as material for the membrane element, it is in this way possible to achieve a greater durability. It is thus possible to prevent the membrane element from shrinking and/or becoming brittle or rigid.

The implantable device according to the invention can be used particularly in the treatment of heart disease in adults, particularly preferably in the treatment of aortic valve incompetence which occurs increasingly with advancing age.

For a more detailed explanation of the invention, illustrative embodiments are described in greater detail below with reference to the drawings, in which.

Figure 1:
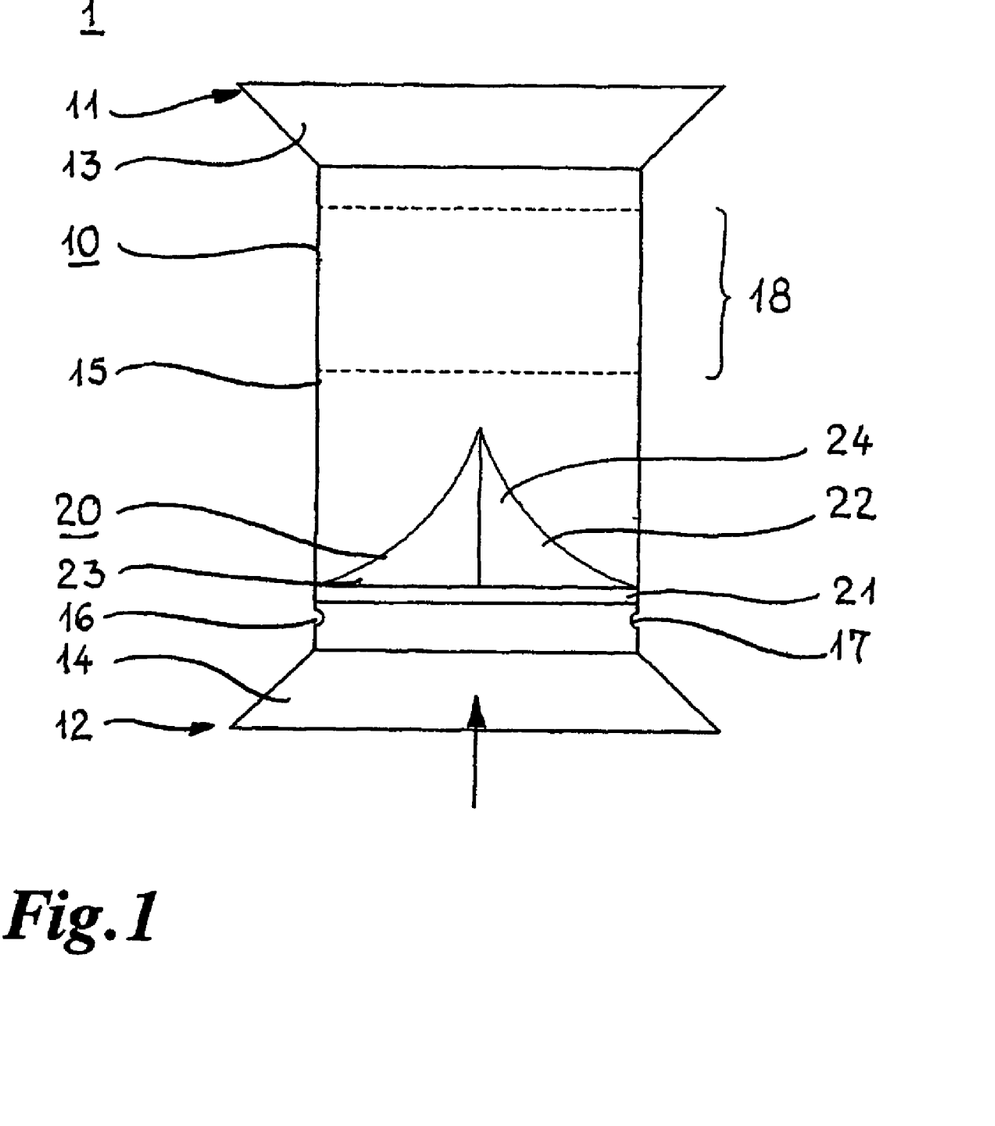
FIG. 1 shows a diagrammatic side view of a first embodiment of an implantable device according to the invention.

FIG. 1 shows a side view of a first embodiment of an implantable device 1 according to the invention. The implantable device 1 has a main body 10 and a membrane element 20. At both its ends 11, 12, the main body 10 is provided with a respective anchoring portion 13, 14. The anchoring portions 13, 14 protrude from the cylindrical central piece 15 of the main body. To make the illustration clearer, the main body is shown without a net structure. However, as can be inferred from the material section of the main body according to FIG. 4, it does have a net structure.

Figure 2:
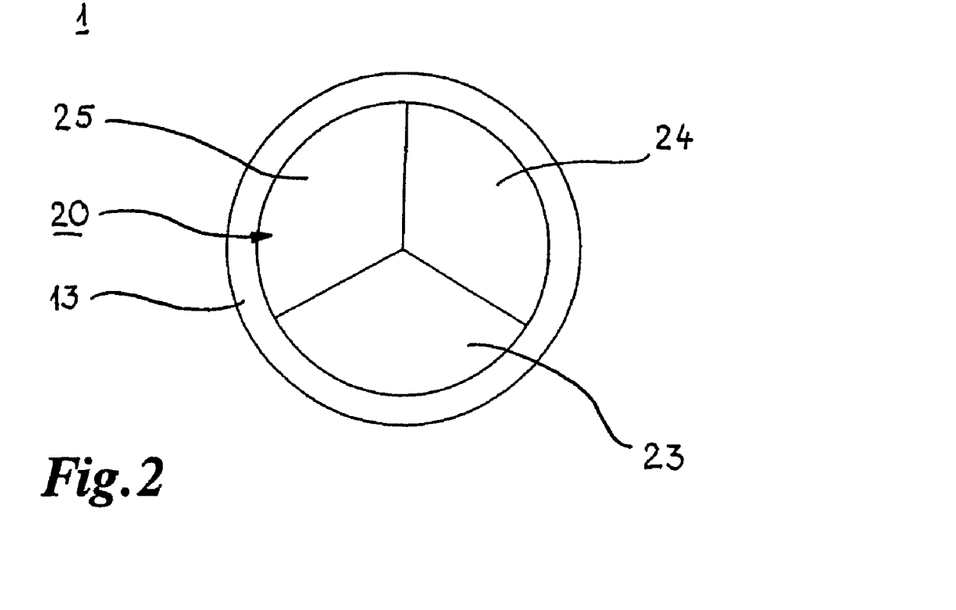
FIG. 2 shows a plan view of the implantable device according to FIG. 1.

The membrane element 20 is inserted in the lower portion of the main body shown in FIG. 1. The membrane element 20 has a ring portion 21 and, connected to the latter, a valve portion 22. The ring portion is arranged along the cylindrical central piece 15 of the main body and is secured there, whereas the valve portion forms three sail elements 23, 24, 25 (see FIG. 2) and extends inward into the main body. The three sail elements 23, 24, 25 form the actual heart valve. They are therefore drawn upward into the main body in such a way that a flow of blood is possible in one direction, but a return flow of blood can be avoided. In this way they assume the function of the natural heart valves, which are likewise intended to prevent a return flow of blood. The direction of flow of the blood is indicated by an arrow.

Slightly below the ring portion 21 of the membrane element, two guide openings 16, 17 are provided in the cylindrical central piece 15 of the main body. Guide wires can be guided through the guide openings 16, 17 so that, upon implantation of the implantable device 1, the latter can be guided and maneuvered into the correct position. The guide wires can either be guided from inside through the guide openings 16, 17 or can be engaged into these from the outside.

Figure 3:
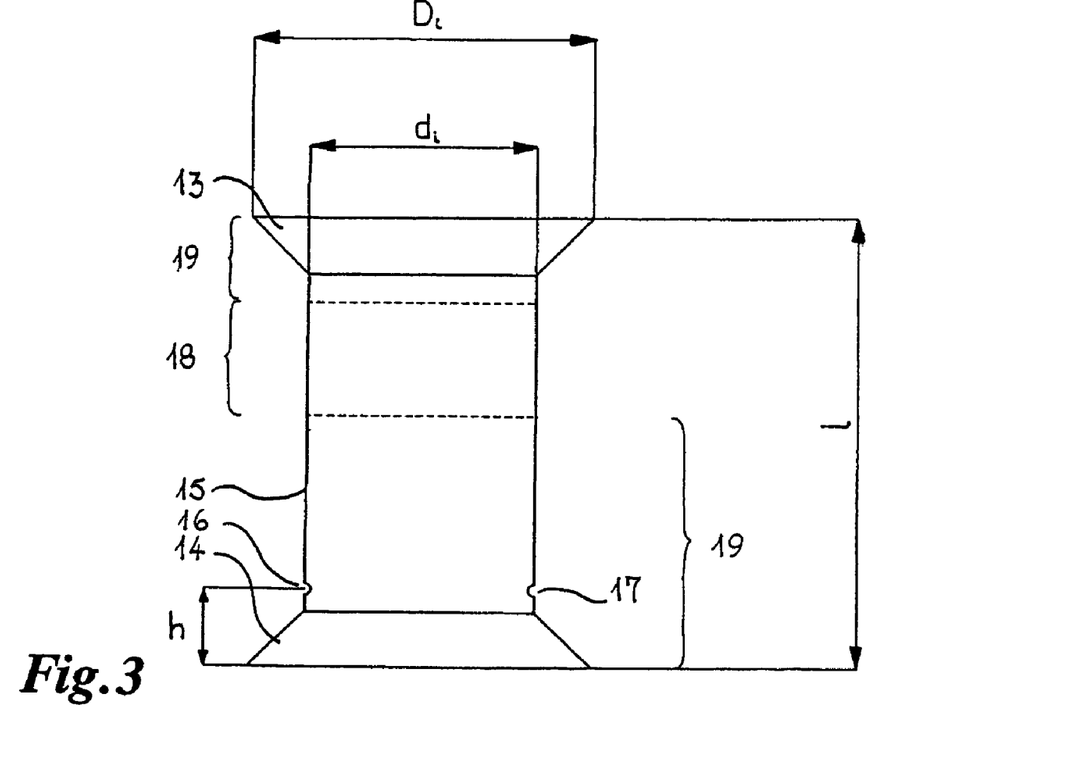
FIG. 3 shows a side view of the implantable device according to FIG. 1, without inserted membrane element.

An area 18 demarcated by broken lines is designed to be more flexible than the other areas 19 (see FIG. 3). The more flexible area 18 can be bent in order to follow a curvature of a vessel, as will be explained in greater detail below with reference to FIG. 3.

The plan view of the implantable device 1 according to FIG. 2 once again shows the membrane element 20 with its three sail elements 23, 24, 25 which between them form an opening for the passage of blood and act as a nonreturn valve. This plan view also shows particularly clearly the protruding anchoring portion 13. The latter is preferably introduced into the aorta and sits there firmly on the wall of the aorta. The other anchoring portion 14 is preferably introduced into the ventricle, in particular the left ventricle, and sits firmly in the latter. This ensures a secure hold against slipping of the implantable device, even in the event of considerable pressure acting on it. For example, a difference between the internal diameter $d_i$ of the cylindrical central piece 15 of the main body and the internal diameter $D_i$ of the anchoring portion of 5 mm guarantees a secure hold both in the ventricle and also inside the aorta. The guide openings preferably have an adequate spacing from the anchoring portions in order to ensure a secure hold of the guide wires in the guide openings, even in the deployed state of the main body, that is to say with the anchoring portions protruding. The spacing h between the outer edge of the anchoring portion 14 and the center of the guide openings 16, 17 is between 5 and 7 mm, for example.

The length of the main body can be chosen shorter than is possible in the prior art, in particular according to DE 101 21 210 A1. The length 1 can be 40 mm for example. Depending on the application, i.e. on the physical conditions of a patient, any other desired dimensions of the main body can be chosen.

In its upper half shown in FIG. 3, the cylindrical central piece 15 of the main body has an area 18 which has a lesser stiffness than the other areas 19. As has already been mentioned above, this more flexible area 18 can particularly advantageously be arranged in the aorta at the location where the latter presents a curvature. This makes it particularly easy to adapt to the shape of the aorta and the implantation site.

Figure 4:
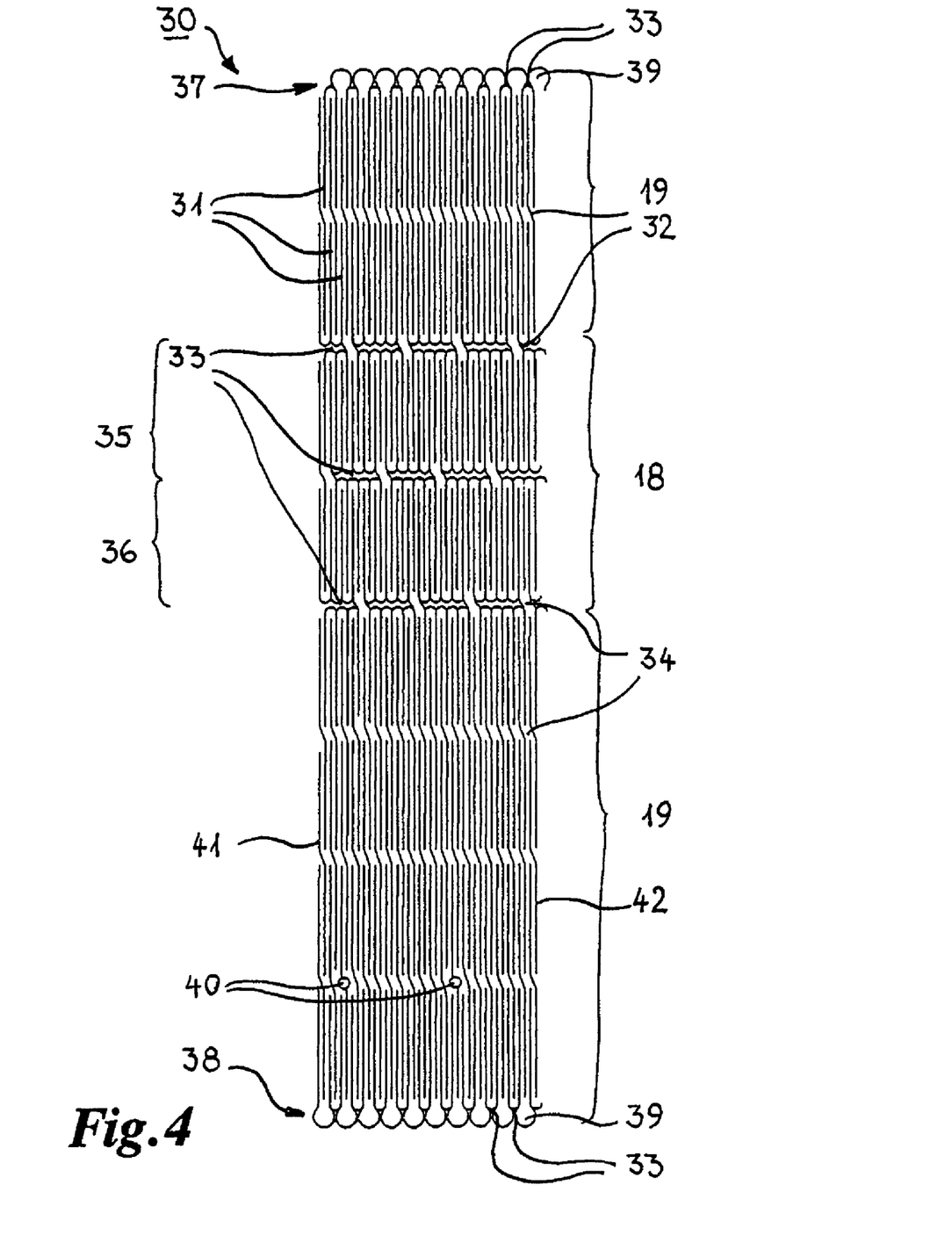
FIG. 4 shows a plan view of a material section for a main body, designed according to the invention, of an implantable device according to the invention.
Figure 5:
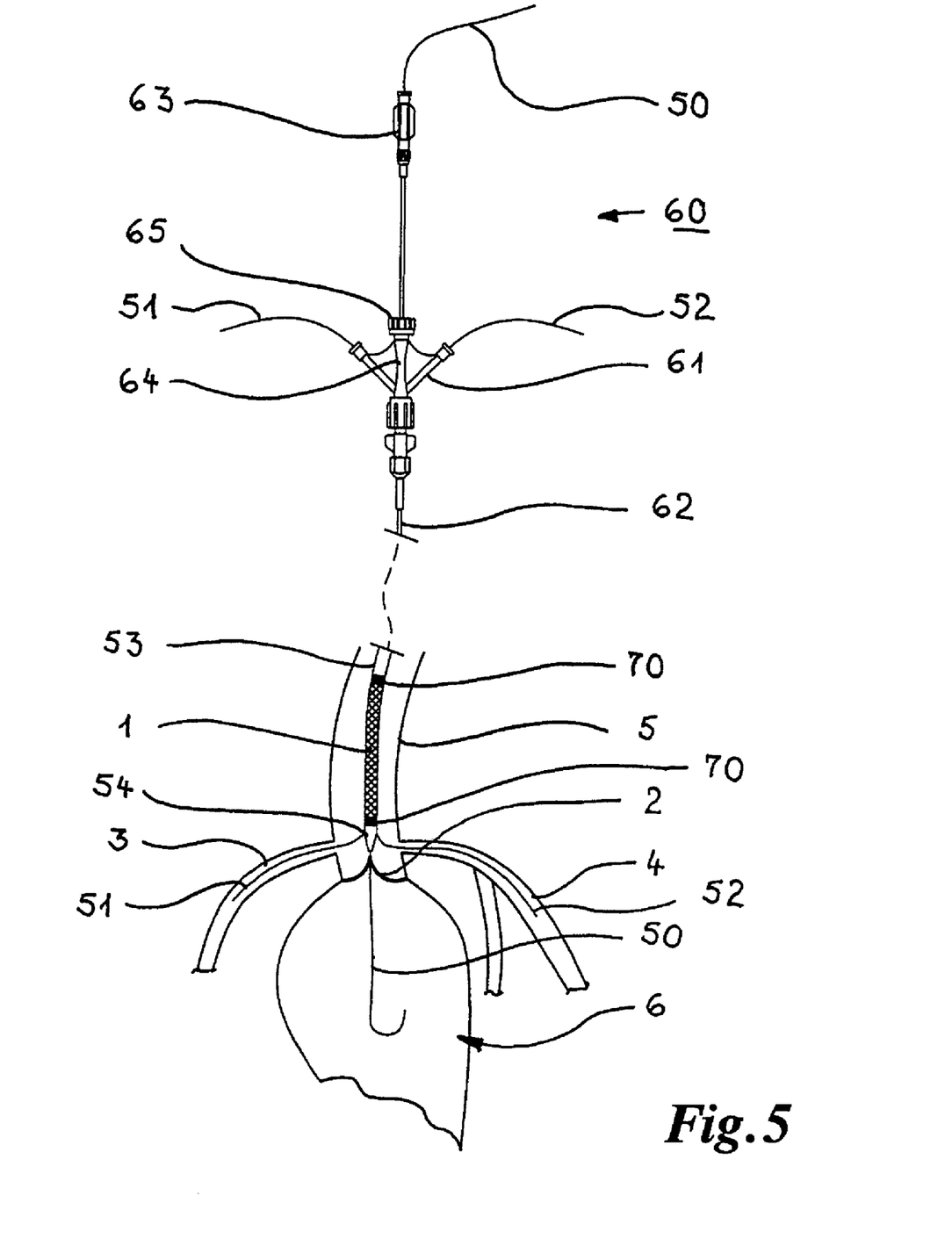
FIGS. 5 to 10 show diagrams of the procedure for implanting an implantable device according to the invention.

FIG. 4 is a plan view of a material section 30 of the main body. The material section has a series of parallel cuts 31 and oblique cuts 32. The oblique cuts in each case alternately connect two parallel cuts to one another. In this way, bridges 34 are formed, so that, when the material section is drawn out, meshes are obtained together with the parallel cuts, with the result that the net structure of the main body can be formed.

In the area of the material section which is intended to form the flexible area 18 of the main body, cuts 33 are additionally provided extending transversely with respect to the parallel cuts. The transversely extending cuts are configured in such a way that parallel cuts arranged next but one are connected to one another. The transversely extending cuts form rounded areas, so that, when the material section is drawn out, no points are formed, but instead only rounded corners of the meshes. The transversely extending cuts 33 mean that the material section is weakened in this area, as a result of which it is more flexible and can be curved in different directions.

Provided between the individual transversely extending cuts 33 there are once again in each case obliquely extending cuts, which again form bridges 34. These bridges on the one hand connect the stiffer areas 19 to the more flexible area 18 and on the other hand connect the two portions 35, 36 of the more flexible area 18 to one another.

The two ends of the main body, that is to say the ends 37, 38 of the material section, have rounded cut elements 39 widened at one end. These rounded cut elements connect next-but-one cuts to one another, and, between these, next-but-one cuts are connected to one another by transversely extending cuts 33. In this way, the meshes of the jacket of the main body can be very easily formed, and yet a traumatic termination at the two ends of the main body can be produced. The risk of injury to the wall of the aorta and/or to an area of the ventricle can thus be substantially avoided.

In some of the obliquely extending cuts 32, punched-out or cut-out holes 40 are additionally provided as guide openings. The holes 40 are not formed in the bridges 34 formed between two obliquely extending cuts, but as partial widening of the cuts. Compared to the hole diameters shown in FIG. 4, it is also possible to choose greater hole diameters, if the guide openings are to be made larger. Additional holes can also be formed in the material section in order to provide additional openings in the area of the origins of the coronary arteries. Adaptation to the particular position of the origins of the coronary arteries can be done without any problem by changing the position of the holes in the material section. This is very simple in a computer-aided cutting technique and can be tailored to the specific patient.

The material chosen for the material section 30 is preferably a metal, in particular a shape-memory material such as nitinol. To generate a cylindrical main body with protruding anchoring portions, the two lateral longitudinal edges 41, 42 are connected to one another in the longitudinal direction of the material section, in particular by soldering or welding or adhesive bonding or by another joining technique. The membrane element can thereafter be introduced into the structure of the main body or applied to the latter in the area of its ring portion 21. The ring portion can either be bonded into the structure of the main body or sewn in, welded or otherwise secured. It is also possible to melt it onto or into the structure of the main body, preferably from both sides of the structure of the main body. Immersing the structure of the main body into a suitable material in order to form the membrane element also proves very advantageous since in this case the structure of the main body is likewise wetted with the material of the membrane element on both sides, thus permitting a very good hold of the membrane element on the main body. If a biological membrane element is used, it is particularly suitable to sew the membrane element into the structure of the main body.

Known techniques are used to shape the main body and to impress the selected shape on the preferably used shape-memory material. The implantable device can then be folded up reversibly to such an extent that it fits into a catheter and can be guided through the latter to the implantation site in a patient's heart and can there be deployed reversibly at the implantation site, so that, in the event of inadequate deployment and/or incorrect positioning, it is possible to retract the implantable device back into the catheter and then reposition it again at the implantation site.

FIGS. 5 to 10 show the procedure for implanting the implantable device 1 in a heart valve, which is here an aortic valve 2. The aortic valve forms the transition from the aorta 5 to the ventricle 6. In this area, first and second coronary vessels 3, 4 branch off from the aorta.

For the implantation procedure, a first guide wire 50 is initially introduced through the aortic valve 2 and into the ventricle 6. Further guide wires 51, 52 are then guided into the coronary vessels 3, 4. The guide wires are in each case also engaged through the main body of the implantable device 1. In the position shown in FIG. 5, the implantable device is in its primary form in a catheter 53. An actuating device 60 is arranged at the proximal end of the catheter. The actuating device is provided with a Y-shaped adapter piece 61. The three guide wires are guided through the latter and separated from one another, as a result of which they can be actuated individually. The middle guide wire 50 is additionally guided through a guide sleeve 62 which ends in a grip piece 63. A central connector piece 64 of the Y-shaped adapter piece additionally has an actuating wheel 65. By means of the actuating wheel 65, the guide sleeve and with it the guide wire 50 can be pushed into the ventricle 6.

Figure 6:
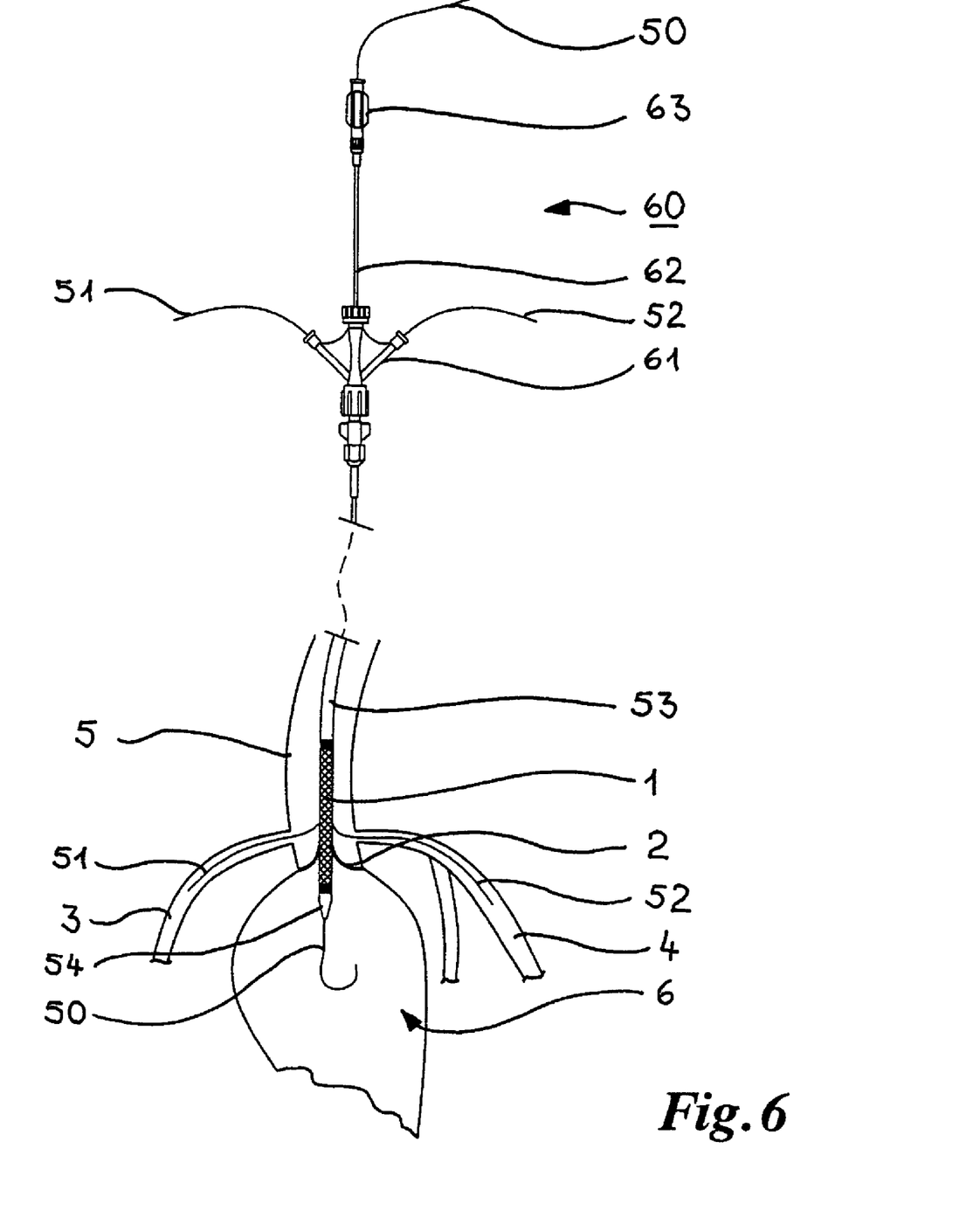

To detect the position of the catheter and in particular of the implantable device by means of imaging equipment, platinum markers 70 are provided on the catheter in the area of both ends of the implantable device. At its distal end, the catheter forms a tip 54. By providing this tip 54, it is particularly easy to guide the catheter through the natural heart valve 2. The catheter guided through the aortic valve 2 is shown in FIG. 6. Here, the implantable device 1 is also pushed partially through the natural heart valve 2.

Figure 7:
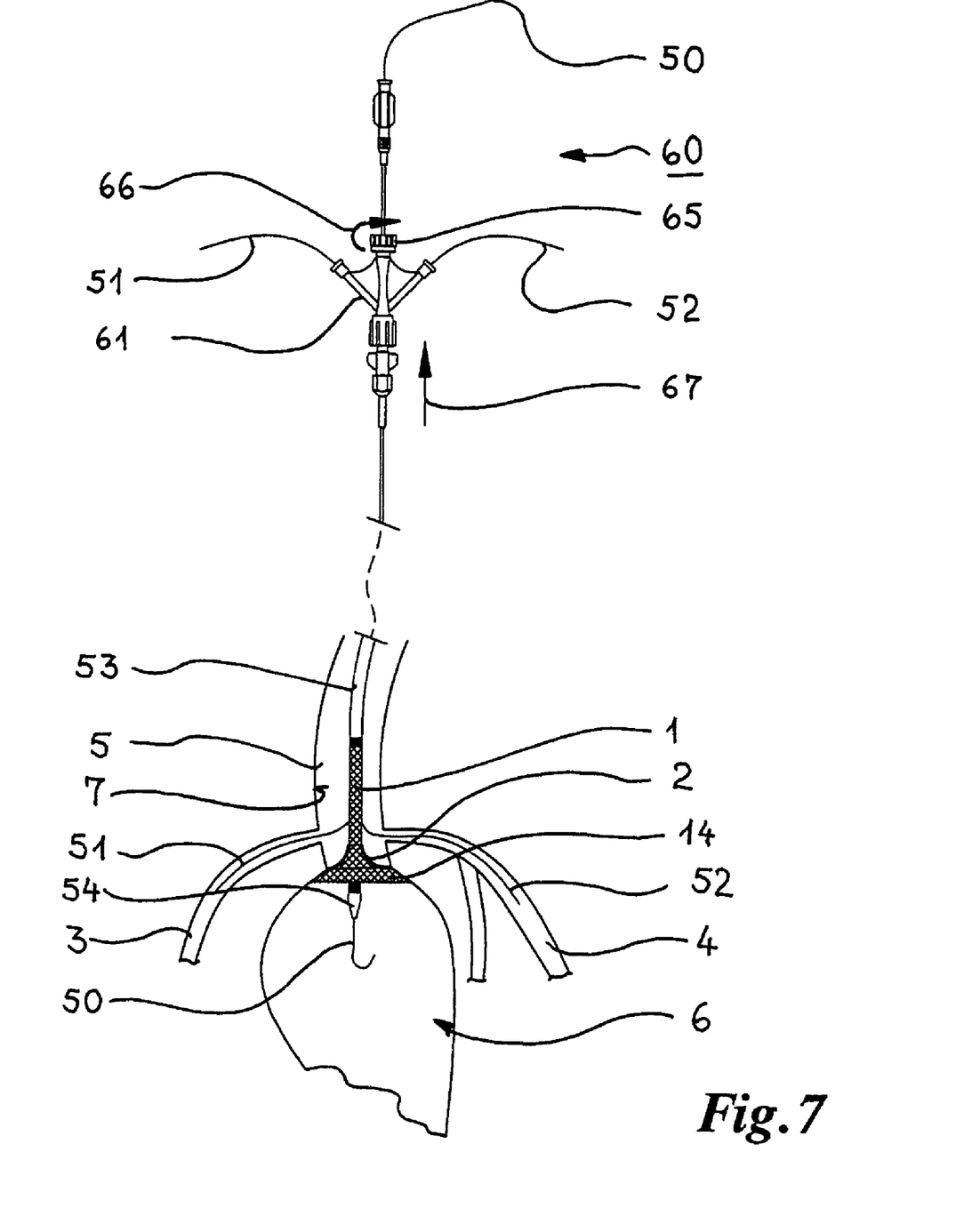

FIG. 7 shows the first step involved in placing the implantable device on the side of the aortic valve facing toward the ventricle. First, the anchoring portion 14 is deployed and secures itself around the aortic valve 2 on the inside of the ventricle 6. To do this, the actuating wheel 65 is turned counterclockwise and at least the middle guide wire 50 is drawn back via the actuating device. This is indicated by the two arrows 66, 67 in FIG. 7.

Figure 8:
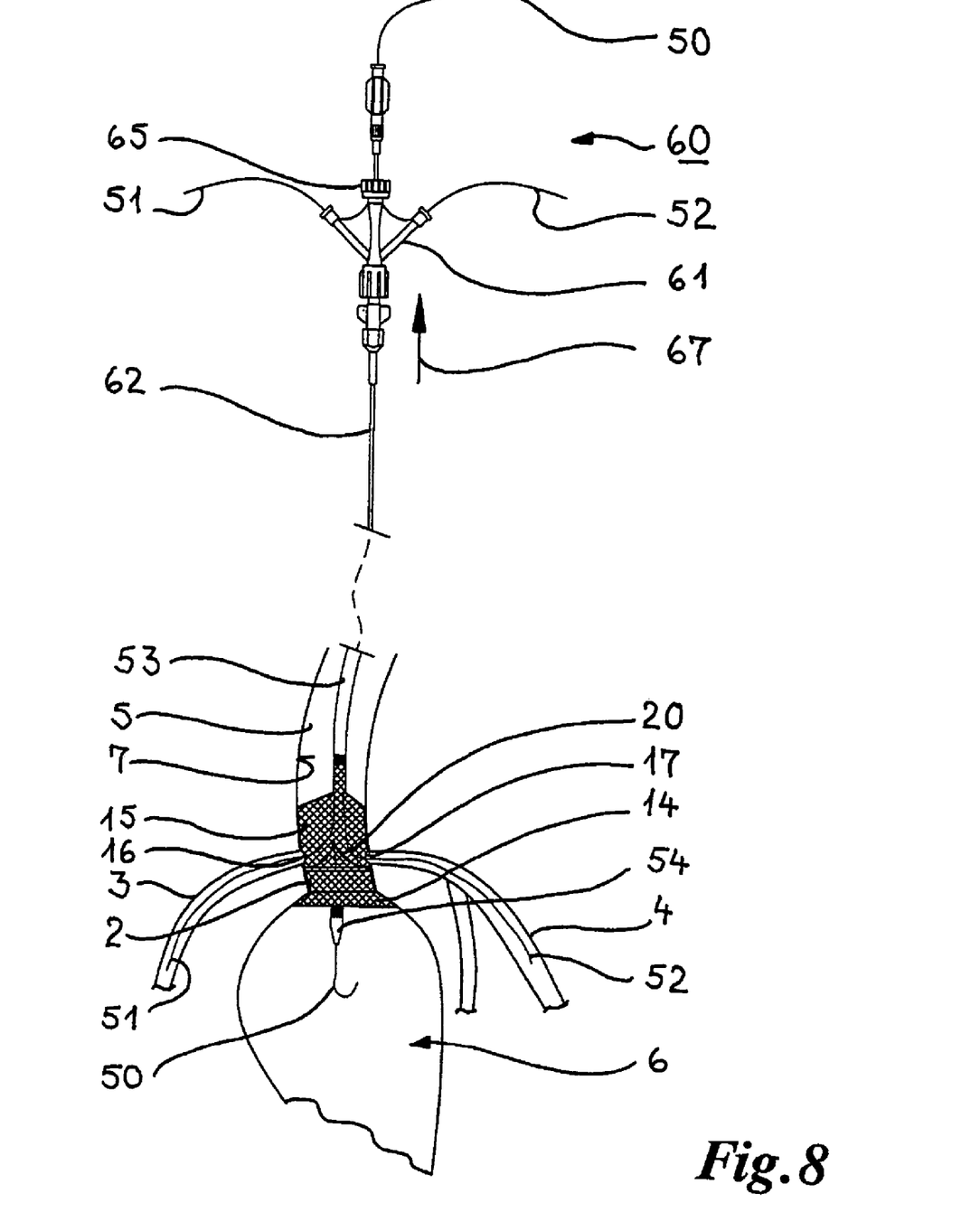
Figure 9:
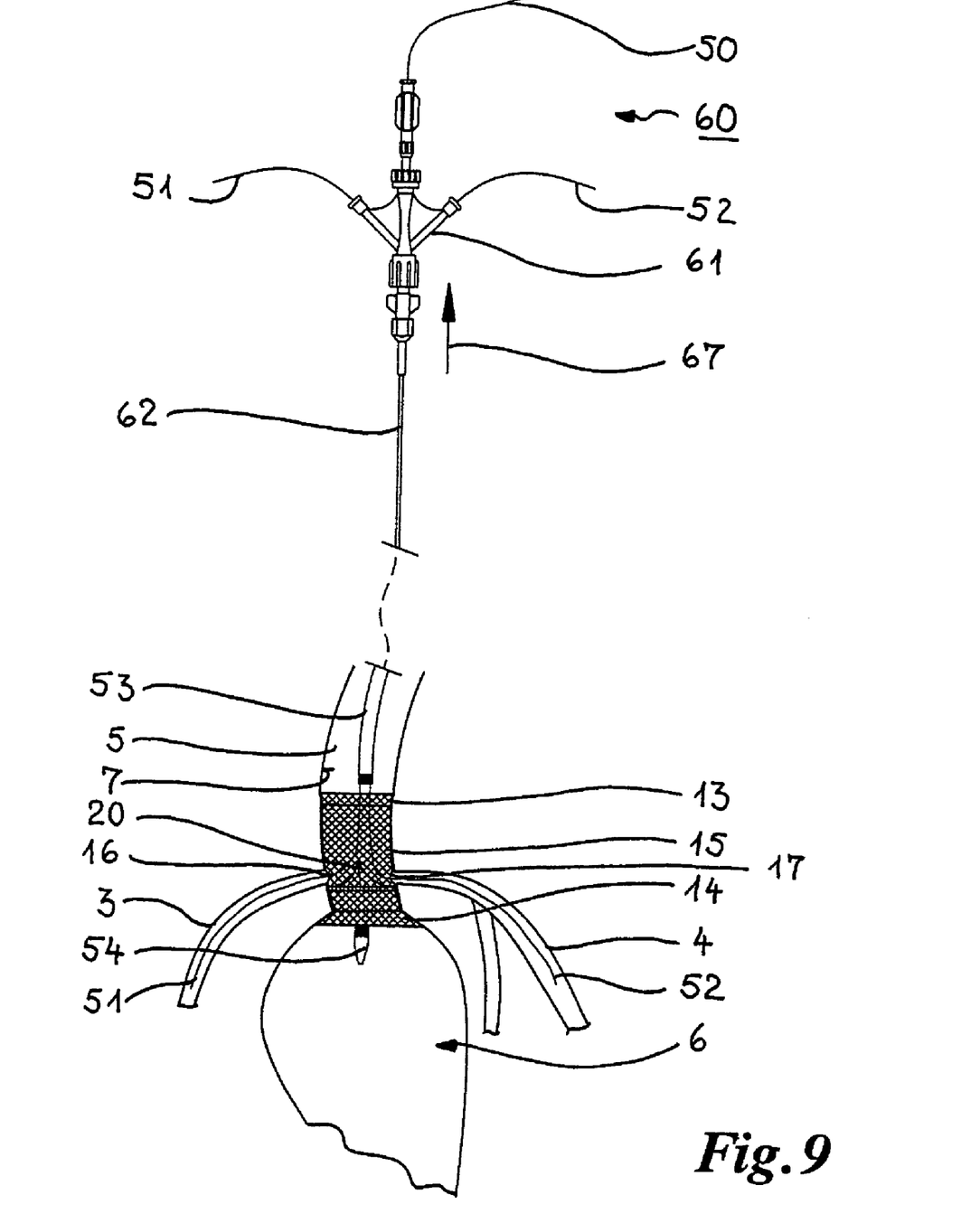
Figure 10:
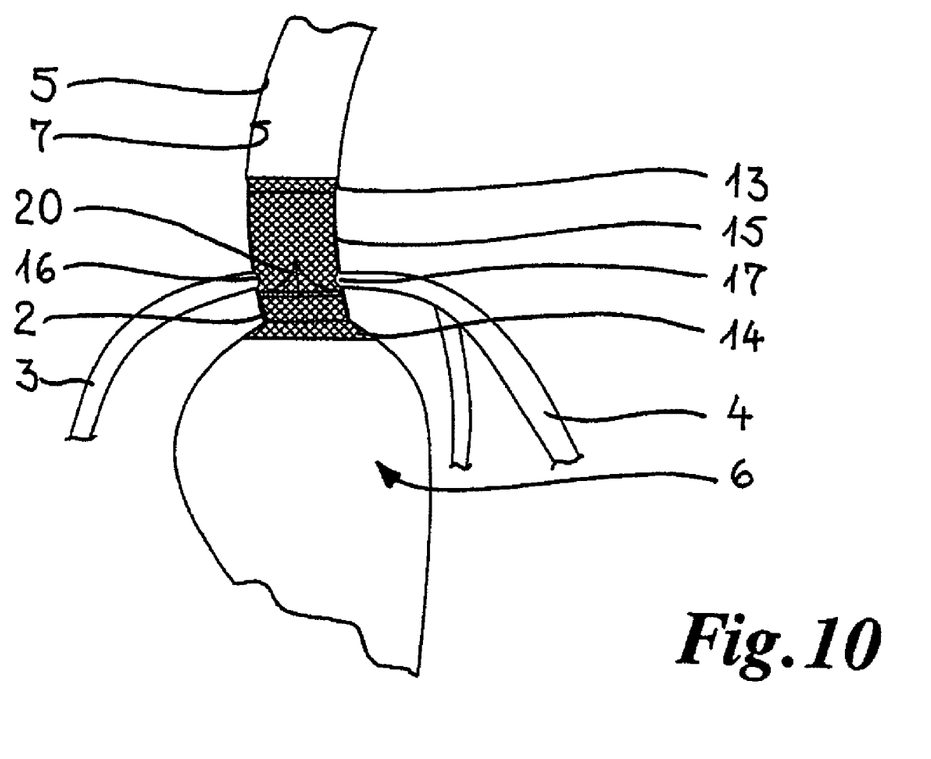

To be able to hold the implantable device with its guide openings 16, 17 exactly positioned in front of the origins of the coronary vessels 3, 4 from the aorta 5, the guide wires 51, 52, as can be seen in FIGS. 8 and 9, initially remain in the coronary vessels 3, 4. In the implantation step illustrated in FIG. 8, a large part of the cylindrical central piece 15 of the main body of the implantable device is already deployed. It therefore now bears against the inside 7 of the aorta 5 in such a way that the natural aortic valve 2 is pressed against the inside 7 of the aorta. The function of the natural aortic valve is now taken over by the membrane element 20 of the implantable device. The latter is now situated in the area of the natural aortic valve, as can be seen from FIGS. 8 and 9.

In the illustration according to FIG. 9, the implantable device has taken up its final position the aorta. Thus, the anchoring portion 13 has also come to bear against the inside 7 of the wall of the aorta. The middle guide wire 50 has already been pulled back into the catheter. After the guide openings 16, 17 have been positioned in alignment with the origins of the coronary vessels 3, 4, the guide wires 51, 52 can also be pulled back into the catheter. Thereafter, it is also possible for the catheter to be pulled back entirely from the implantation site, as is shown FIG. 10. Flow of blood and opening and closing with the artificial aortic valve is now possible. By adaptation of the width of opening of the guide openings 16, 17, the implantable device does not create any obstruction, even in the area of the origins of the two coronary vessels 3, 4, so that here too blood is able to flow free of any barrier.

In addition to the embodiments described above and shown in the drawings, many others are also possible in which the implantable organ valve device in each case comprises, at the ends of the main body of the implantable device, protruding anchoring portions for anchoring the device in an organ and/or a vessel in the human or animal body, or in which the main body for the device is made essentially in one piece, so that it is possible to create a more compact device, and achieve a more efficient production and simpler adaptation to the physical circumstances of individual patients, than is possible in the prior art.

The invention claimed is:

1. Implantable device for use in a human and/or animal body for replacement of an organ valve, comprising:
   an expandable, elongate main body having a longitudinal axis and being substantially cylindrical in shape about said axis, said body including a first end and a second end each provided with an opening;
   at least one outwardly protruding anchoring portion disposed proximate at least one of said first and second ends of said main body;
   an expandable membrane element provided with at least one opening, said membrane element disposed within the main body and having a valve portion and a ring portion secured to the main body; and
   said main body and said membrane element together movable between a first condition in which said main body and said membrane element together define a first cross sectional area, and a second, deployed condition in which said main body and said membrane element together define a second cross sectional area greater than said first cross sectional area.

2. Implantable device according to claim 1, wherein the protruding anchoring portion extends around the circumference of the main body.

3. Implantable device according to claim 1, wherein the device has areas of different stiffness.

4. Implantable device according to claim 3, wherein at least one area of lesser stiffness is arranged between at least two areas of greater stiffness.

5. Implantable device according to claim 4, wherein the at least one area of lesser stiffness is provided in the main body.

6. Implantable device according to claim 1, wherein at least one guide opening is provided for the passage of guide wires for the implantation of the device.

7. Implantable device according to claim 6, wherein the at least one guide opening is arranged near the membrane element.

8. Implantable device according to claim 6, wherein the at least one guide opening has a diameter substantially corresponding to the opening width of the origins of the coronary arteries to be covered by the device.

9. Implantable device according to claim 1, wherein the main body includes markings detectable by imaging techniques.

10. Implantable device according to claim 1, wherein one or more additional openings are provided in the area of the device covering the origins of the coronary arteries after implant of the device.

11. Implantable device according to claim 1, wherein the membrane element is made of a material selected from the group consisting of synthetic, biological, and polyurethane materials.

12. Implantable device according to claim 11, wherein the membrane element is provided with a coating for biostability.

13. Implantable device according to claim 1, wherein the membrane element is provided with a coating for biostability.

14. Implantable device according to claim 1, wherein the main body is made of a material selected from the group consisting of biocompatible material, a metal alloy, stainless steel, plastics, polycarbonate, a shape-memory material, and nitinol.

15. Implantable device according to claim 14, wherein the material of the main body is treated at least in one section by chemical and/or mechanical means, in particular by etching, electropolishing, microsectioning or otherwise, to produce different degrees of stiffness.

16. Implantable device according to claim 1, wherein the main body and the membrane element are connectable or connected to one another in a process selected from the group consisting of adhesive bonding, welding, sewing, melting, and immersion.

17. Implantable device according to claim 1, wherein the main body is substantially of one piece.

18. Implantable device according to claim 17, wherein the main body is cut and/or punched from a piece of material and/or separated therefrom by another method of separation.

19. Implantable device according to claim 1, wherein the main body is cut and/or punched from a piece of material and/or separated therefrom by another method of separation.

20. Implantable device for use in a human and/or animal body for replacement of an organ valve, comprising:
   an elongate main body having a first end and a second end each provided with an opening; and
   a membrane element provided with at least one opening, said device having a deployed configuration having a relatively larger cross sectional area, and a non-deployed configuration having a relatively smaller cross sectional area, said device convertible from the non-deployed configuration to the deployed configuration by application of force against elastic material forces of the main body, wherein at least one of the first end and the second end of the main body has an outwardly protruding anchoring portion for anchoring the device in the organ and/or a vessel;
   wherein the main body is substantially of one piece;
   wherein the main body is cut and/or punched from a piece of material and/or separated therefrom by another method of separation;
   wherein the material section comprises parallel cuts and alternating subsequent cuts extending obliquely.

21. Implantable device according to claim 20, wherein cuts extending obliquely with respect to the parallel cuts are provided for producing areas of different stiffness.

22. Implantable device according to claim 20, wherein the main body comprises cut elements with widened and rounded ends for producing atraumatic ends of the main body.

23. Implantable device for use in a human and/or animal body for replacement of an organ valve, comprising:
   an elongate main body having a first end and a second end each provided with an opening;
   a membrane element provided with at least one opening, said device having a deployed configuration having a relatively larger cross sectional area, and a non-deployed configuration having a relatively smaller cross sectional area, said device convertible from the non-deployed configuration to the deployed configuration by application of force against elastic material forces of the main body, wherein at least one of the first end and the second end of the main body has an outwardly protruding anchoring portion for anchoring the device in the organ and/or a vessel; and
   a ring portion secured to the main body and connected to a valve portion, the valve portion associated with the membrane element and disposed within the main body;

wherein the main body comprises cut elements with widened and rounded ends for producing atraumatic ends of the main body.

24. Implantable device according to claim 20, wherein at least one hole is provided in the area of the obliquely extending cuts.

25. Implantable device for use in a human and/or animal body for replacement of an organ valve, comprising:
   an elongate main body having a first end and a second end each provided with an opening; and
   a membrane element provided with at least one opening, said device having a deployed configuration having a relatively larger cross sectional area, and a non-deployed configuration having a relatively smaller cross sectional area, said device convertible from the non-deployed configuration to the deployed configuration by application of force against elastic material forces of the main body, wherein at least one of the first end and the second end of the main body has an outwardly protruding anchoring portion for anchoring the device in the organ and/or a vessel;
   wherein the membrane element has a ring portion and, connected thereto, a valve portion;
   wherein the valve portion comprises three sail elements.

26. Implantable device according to claim 25, wherein the membrane element is made of a material selected from the group consisting of synthetic, biological, and polyurethane material.

27. Method for producing an implantable device according to claim 1, comprising the steps of:
   cutting and/or punching a main body from a piece of material;
   bending the main body into a substantially cylindrical body;
   inserting a membrane element into the substantially cylindrical main body and connected therewith; and
   securing the ring portion to the main body, the ring portion connected to the valve portion associated with the membrane element.

28. Method according to claim 27, wherein the material cut is carried out so as to produce a continuous net structure of the substantially cylindrical main body, wherein the material includes at least partly different mesh sizes.

29. Method for implanting an implantable device according to claim 1 in the heart of a human or animal body, wherein guide wires are guided through guide openings of the main body, the guide wires being advanced by a probe to the site of implantation in the heart, the guide wires being at least partly pushed into the coronary vessels, the device then being advanced in the non-deployed configuration via a catheter into the body of the patient to the site of implantation in the heart, where the device is expanded and oriented with respect to the origins of the coronary vessels from the heart with the aid of the guide wires.

30. Method according to claim 29, wherein the device is pushed so far into the area of the cardiac valve, especially the aortic valve, that the natural valve is pressed against the wall of the vessel and is held there by the device.

31. Method according to claim 29, wherein the at least one guide wire and/or the implantable device is introduced into the body via the aorta carotis or arteria axillaris.

32. Method according to claim 29, wherein the main body of the device is oriented such that the protruding anchoring portion at the first end protrudes into the heart ventricle, especially the left heart ventricle, and the protruding anchoring portion at the second end is clamped to the wall of the vessel, especially the aortic wall.

33. Method according to claim 29, wherein the at least one guide wire is passed through the main body and/or arranged at the outside of the main body.

34. Implantable device for use in a human and/or animal body for replacement of an organ valve, comprising:
   an elongate main body having a first end and a second end each provided with an opening; and
   a membrane element provided with at least one opening, said device having a deployed configuration having a relatively larger cross sectional area, and a non-deployed configuration having a relatively smaller cross sectional area, said device convertible from the non-deployed configuration to the deployed configuration by application of force against elastic material forces of the main body, wherein at least one of the first end and the second end of the main body has an outwardly protruding anchoring portion for anchoring the device in the organ and/or a vessel;
   wherein the membrane element has a ring portion and, connected thereto, a valve portion;
   wherein the main body comprises cut elements with widened and rounded ends for producing atraumatic ends of the main body.

* * * * *